United States Patent
Rama Krishna et al.

(10) Patent No.: US 7,879,584 B2
(45) Date of Patent: Feb. 1, 2011

(54) **PROCESS FOR INCREASED PATCHULOL CONTENT IN ESSENTIAL OIL OF *POGOSTEMON CABLIN***

(75) Inventors: Sonti Venkata Rama Krishna, Maharashlir (IN); Harshad Velankar, Maharashlir (IN)

(73) Assignee: Reliance Life Sciences PVT, Ltd., Navi Mumbai (IN)

( * ) Notice: Subject to any disclaimer, the term of this patent is extended or adjusted under 35 U.S.C. 154(b) by 0 days.

(21) Appl. No.: 11/707,721

(22) Filed: Feb. 15, 2007

(65) Prior Publication Data

US 2007/0298482 A1    Dec. 27, 2007

Related U.S. Application Data

(63) Continuation of application No. PCT/IN2007/000014, filed on Jan. 12, 2007.

(30) Foreign Application Priority Data

Jan. 16, 2006    (IN) .......................... 59/MUM/2006

(51) Int. Cl.
C12P 7/64    (2006.01)
C12P 1/00    (2006.01)
C12P 7/00    (2006.01)
C12N 1/00    (2006.01)

(52) U.S. Cl. .................. 435/134; 435/41; 435/132; 435/243; 435/254.1

(58) Field of Classification Search ........................ None
See application file for complete search history.

(56) References Cited

U.S. PATENT DOCUMENTS

| 4,037,609 | A * | 7/1977 | Newton et al. .............. 131/308 |
| 4,686,187 | A * | 8/1987 | Sakai et al. ................. 435/275 |
| 6,338,861 | B1 | 1/2002 | Gozu et al. |
| 2006/0216723 | A1 * | 9/2006 | Diaz et al. ..................... 435/6 |

FOREIGN PATENT DOCUMENTS

GB    1586859 A    3/1981

OTHER PUBLICATIONS

Gueho, E. and Smith, M.T. "DSM 12017—*Trichosporon mucoides*" Deutsche Sammlung von Mikroorganismen und Zellkulturen (DSMZ) GmbH [online], 2004, [retrieved Mar. 27, 2009]. Retrieved from the Internet <URL:http://www.dsmz.de/microorganisms/html/strains/strain.dsm012017.html>, 3 pages.*

Microbial Type Culture Collection & Gene Bank (MTCC) "All Cultures: Alphabetical Order" MTCC [online], [retrieved Mar. 27, 2009]. Retrieved from the Internet <URL: http://www.imtech.res.in/mtcc/alpha.html>, pp. (i) and 1-149.*

(Continued)

*Primary Examiner*—Christopher R Tate
*Assistant Examiner*—Aaron J Kosar
(74) *Attorney, Agent, or Firm*—Mintz Levin Cohn Ferris Glovsky and Popeo, P.C.; Ivor R. Elrifi; Christina K. Stock, Esq.

(57) ABSTRACT

A process is provided for improving sensory properties of essential oils by treatment and incubation with a microbial culture during the extraction process. A method for increasing the patchulol content in essential oil extracted from leaves of *Pogostemon cablin* is provided, comprising contacting a dried patchouli biomass with microbial cultures, incubating the patchouli biomass under conditions suitable for allowing the increase in the patchulol content and extracting the oil. This process results in increased patchulol content without decreasing the overall oil yields. The patchouli oil also has enriched aroma.

24 Claims, 7 Drawing Sheets

OTHER PUBLICATIONS

Nikitin, G. A.; Sadovnikova, T. A. "Selection of productive feed yeast strains for growth on syrupy malt residues" Trudy, Ukrainskii Nauchno-Issledovatelskii Institut Spirtovoi i Likero-Vodochnoi Promyshlennosti. 1965, 10, pp. 89-94 and CAS Abstract.* de Jong, A.W.K. "Some Observations on Essential Oil Plants and their Essences" Recueil des Travaux Chimiques des Pays-Bas et de la Belgique, 1912, 30, pp. 211-219. (CAS Abstract).*

Anonymous, "Commodity Bulletin on Aromatic: Patchouli - Post Harvest Technology", Natl. Horticulture Board, Ministry of Agriculture, Gov't of India (Oct. 7, 2001), 1 page.

Arctander, S., "Patchouli Oil", in *Perfume and Flavor materials of Natural Origin*, Allured Publishing Corp., Carol Stream, IL., pp. 508-511 (1994).

Bown, D., "Pogostemon" in *The Herb Society of America New Encyclopedia of Herbs and Their Uses*, Dorling Kindersley Ltd., London, p. 325 (2001).

Buckle, J., "Infection", in *Clinical Aromatherapy Essential Oils in Practice*, Second Ed., Churchill Livingstone, NY, Ch. 9, pp. 162-200 (2003).

Cech, M., "Aromatherapy Favorites: Patchouli Essential Oil", Ezinearticles.com (2005) 3 pages.

Haze et al., "Effects of Fragrance Inhalation on Sympathetic Activity in Normal Adults", *Jpn. J. Pharmacol.*, 90:247-253 (2002).

Keville et al., "Extracting Essential Oils/Chemistry of Essential Oils", in *Aromatherapy A Complete Guide to the Healing Art*, The Crossing Press, Freedom, CA, Ch. 12-13, pp. 120-131 (1995).

Keville et al., "Guidelines for Using Essential Oils and Herbs", in *Aromatherapy A Complete Guide to the Healing Art*, The Crossing Press, Freedom, CA, Ch. 4, pp. 20-28 (1995).

Leung et al., "Patchouly Oil", in *Encyclopedia of Common Natural Ingredients Used in Food, Drugs, and Cosmetics*, 2nd Ed., John Wiley & Sons, Inc., New York, pp. 411-413 (1996).

McMahon, C., "Patchouli", White Lotus Aromatics Newsletter - Patcholi, (Jan. 24, 2001) 14 pages.

Munck et al., "Purification and Characterization of the Sesquiterpene Cyclase Patchoulol Synthase From *Pogostemon cablin*", *Arch. Biochem. Biophys.*, 282(1):58-64 (1990).

Nurhayati, O., "Fermentation Optimization of Condition and from Essential Oil Extraction Patchouli", *Ganesha Digital Library, School of Science and Technology a member of the IndonesiaDLN Institut Teknologi Bandung Network*, (Apr. 18, 2005) (English Translation), 4 pages.

Oyen et al., "Pogostemon Desf.", in *Plant Resources of South-East Asia No. 19 Essential-oil plants*, Prosea Foundation, Bogor, Indonesia, pp. 151-157 (1999).

Shin et al., "Biotransormation of benzeldehyde to L-phenylacetylcarbinol, an intermediate in L-ephedrine production, by immobilized *Candida utilis*", *Appl. Microbiol. Biotechnol.*, 44:7-14 (1995).

Tucker, A. O., "Patchouli - Pogostemon", in *The Big Book of Herbs*, Interweave Press, Inc., Loveland, CO, pp. 484-489 (2000).

Yen, K., "Crude and prepared", in *The Illustrated Chinese Materia Medica*, SMC Publishing, Inc., Taipei, China, p. 193 (1992).

* cited by examiner

Figure 3

| 14 | 8.93 | 33.77 | C:\DATABASE\NBS75K.L | | | |
|---|---|---|---|---|---|---|
| | | | Patchouli alcohol | 28249 | 005986-55-0 | 98 |
| | | | 1(2H)-Naphthalenone, octahydro-4a, | 28215 | 001803-39-0 | 30 |
| | | | 1H-Purine-2,6-dione, 3,7-diethyl-3 | 28003 | 053432-05-6 | 20 |
| 15 | 8.99 | 0.90 | C:\DATABASE\NBS75K.L | | | |
| | | | Longifolenaldehyde | 27715 | 019890-84-7 | 38 |
| | | | 7-Oxabicyclo[4.1.0]heptane, 1-meth | 10364 | 001195-92-2 | 32 |
| | | | Bicyclo[3.1.0]hex-3-en-2-one, 4-me | 66773 | 024545-81-1 | 22 |

Figure 6

| 11 | 8.77 | 3.71 | C:\DATABASE\NBS75K.L | | | |
|----|------|------|----------------------|--|--|--|
| | | | Azulene, 1,2,3,5,6,7,8,8a-octahydr | 23929 | 003691-11-0 | 62 |
| | | | 1,4-Methano-1H-indene, octahydro-4 | 23977 | 003650-28-0 | 35 |
| | | | Cyclopropa[d]naphthalen-2(4aH)-one | 23869 | 004677-90-1 | 30 |
| 12 | 8.89 | 45.64 | C:\DATABASE\NBS75K.L | | | |
| | | | Patchouli alcohol | 70636 | 005986-55-0 | 99 |
| | | | 1H-Purine-2,6-dione, 3,7-diethyl-3 | 28003 | 053432-05-6 | 30 |
| | | | 1(2H)-Naphthalenone, octahydro-4a, | 28215 | 001803-39-0 | 25 |
| 13 | 9.13 | 0.82 | C:\DATABASE\NBS75K.L | | | |
| | | | 1,2,4-Trimethoxybenzene | 14475 | 000135-77-3 | 47 |
| | | | Benzene, [1-(2,4-cyclopentadien-1- | 14809 | 002320-32-3 | 40 |
| | | | 1-Methoxy-2-methyl-4-(methylthio)b | 14454 | 050390-78-8 | 38 |

PROCESS FOR INCREASED PATCHULOL CONTENT IN ESSENTIAL OIL OF *POGOSTEMON CABLIN*

RELATED APPLICATIONS

This application is a continuation of PCT Patent Application Serial No. PCT/IN07/00014 filed Jan. 12, 2007, which claims priority of Indian patent application No.: 59/MUM/2006 filed Jan. 16, 2006, the contents of each of which are incorporated by reference herein in their entirety.

TECHNICAL FIELD OF THE INVENTION

The present invention relates to methods for enhancing sensory properties of oil extracted from a plant by treatment with microbial isolates during extraction. Specifically, the invention relates to incubation of patchouli biomasses with microorganisms during the extraction process such that patchulol content of the extracted oil is increased without decrease in the overall essential oil yields. More specifically, the invention relates to preparation of patchouli oil with an improvement in the sensory characteristics of the patchouli oil.

BACKGROUND OF THE INVENTION

Patchouli (*Pogostemon cablin*) is a member of the mint family. The patchouli plant, or *Pogostemon cablin*, is an upright, bushy, evergreen perennial herb with lightly fragrant leaves, and white, violet-marked flowers. (Bown D. The Herb Society of America New Encyclopedia of Herbs and Their Uses. London: Dorling Kindersley Ltd.; 2001; Leung A Y, Foster S, eds. Encyclopedia of Common Natural Ingredients Used in Food, Drugs, and Cosmetics. 2nd ed. New York: John Wiley and Sons, Inc; 1996.) Native to tropical Asian countries, patchouli is widely cultivated all over the tropics and subtropics including Indonesia, the Philippines, Malaysia, India, southern China, Seychelles, and Brazil. (Bown 2001; Leung 1996; Oyen L P A, Dung N X, eds. Plant Resources of South-East Asia: No 19—Essential-oil plants. Bogor, Indonesia: Prosea Foundation; 1999).

Patchouli oil is conventionally distilled from fermented leaves. (Keville K, Green M. Aromatherapy: A Complete Guide to the Healing Art. Freedom, Calif.: The Crossing Press; 1995.) Other *Pogostemon* species as well as similar species produce inferior oils. (Bruneton J, ed. Pharmacognosy, Phytochemistry, Medicinal Plants. 2nd ed. Paris: Lavoisier; 1999.) The best quality oil is produced from plant materials harvested near plantations where there is less chance of damage to plant materials prior to processing. (Grieve M. A Modern Herbal. Vol. 2. New York: Dover Books; 1971.) Patchouli oil scent has staying power and is perceptible for weeks or months. (Arctander S. Perfume and Flavor Materials of Natural Origin. Carol Stream, Ill.: Allured Publishing Corporation; 1994; Tucker A O, Debaggio T. The Big Book of Herbs. Loveland, Colo.: Interweave Press; 2000) At high concentrations, patchouli scent can be sickeningly sweet, but a strong aroma is a sign of superior quality. (Arctander 1994; Yen K Y. The Illustrated Chinese Materia Medica: Crude and Prepared. Taipei, Taiwan: SMC Publishing Inc; 1992.)

Patchouli has a long history in southern Asia and the Far East as incense, body and garment perfume, and insect and leech repellent. (Oyen 1999) Ink in China and India was once perfumed with patchouli. (Oyen 1999; Arctander 1994).

The major use for patchouli oil is in perfumery. It is also an ingredient in toiletries, cosmetics, breath fresheners, incense, insecticides, disinfectants, and commercial food flavoring. (Bown 2001) Patchouli is one of the most widely used ingredients in perfumes (Leung 1996) and is often the fundamental note in oriental-type perfumes. (Oyen 1999) It is employed as a fragrance component in cosmetic preparations, soaps, and hair removal creams (Leung 1996) because of its masking effect on noxious odors. (Oyen 1999) Patchouli was used in a breath freshener popular during Prohibition called Sen-Sen. (Arctander 1994)) It is a pest deterrent used to keep wool moths out of Indian shawls and rugs. (Keville 1995) Patchouli essential oil is used in flavoring chewing gum, baked goods, and candy, (Facciola S. Cornucopia: A Source Book of Edible Plants. Vista, Calif.: Kampong Publications; 1990) nonalcoholic and alcoholic beverages, desserts, puddings, meat and meat products. (Leung 19946) It has recently been added to low-tar cigarettes and tobacco for flavor. (Oyen 1999) Fresh leaves are sometimes used as seasoning (Yen 1992) and added to potpourri. (Bown 2001)

Historically patchouli has been used to reduce appetite, water retention, exhaustion, and inflammation (Keville 1995) and is said to be a good tonic for veins. (Schnaubelt K, Beasley J M, trans. Advanced Aromatherapy: The Science of Essential Oil Therapy. 1st ed. Rochester, Vt.: Healing Arts Press; 1998.). It has cosmetic and skin uses as a cell rejuvenator and antiseptic. (Keville 1995) It has traditionally been used to treat acne, eczema, inflamed, cracked or mature skin, dandruff, athlete's foot, varicose veins, hemorrhoids, and impetigo. (Bown 2001; Keville 1995) Patchouli has been used for emotional disorders such as nervousness, depression, insomnia, and has also been employed as an aphrodisiac. (Keville 1995) In the East, patchouli oil has been used to prevent spread of infection (Bown 2001) due to its antifungal and antibacterial properties. (Buckle J. Clinical Aromatherapy: Essential Oils in Practice. Philadelphia: Elsevier Science; 2003) In traditional Chinese medicine, patchouli is used in combination with other herbs to provide relief for colds and flu, fever and chills, headache, nausea, vomiting, diarrhea, abdominal pain, malarial and dysenteric disease, and bad breath. (Leung 1996; Tucker 2000).

In aromatherapy, patchouli oil is utilized as a relaxant (Oyen 1999) for nervous exhaustion, depression, stress-related complaints, and low libido. (Bown 2001). In one study, inhaling patchouli essential oil produced a decreased response in the sympathetic nervous system; it lowered systolic blood pressure. (Haze S, Sakai K, Gozu Y. Effects of fragrance inhalation on sympathetic activity in normal adults. Jpn J Pharmacol. 2002 November; 90(3):247-253.)

Essential oils are highly concentrated substances extracted from various parts of aromatic plants and trees. These oils are the result of secondary metabolism of the plant and they form the very basis of the flavor and fragrance industry. The aromatic plants and oils have been used for thousands of years dating back to ancient civilizations that used them to heal, enhance, soothe and excite the body and spirit.

Nikiforov et al; discloses that (−)-patchoulol is the predominant odor component of patchouli oil by using chiral phase gas chromatography combined with a 'sniffing-technique'. (Nikiforov et al; 1986 (±)-Patchouli alcohol, the dominant odor component of the patchouli oil; Chemical Monthly 117(8) 1095-1098).

With an increasing trend for preference of natural products, demand for natural fragrances and flavorings such as patchouli continues to grow, despite market competition by synthetic substitutes which have the advantages of lower production costs, stable pricing and regular supply. There is no natural method employed for increasing the patchulol content in dried leaves. Essential oil extracted from *Pogostemon* sp. with higher patchulol content is highly valued. Most of the sources generate oils having moderate (35-42% w/v) concentrations of patchulol content.

Patchouli oil is extracted by steam distillation of non-fermented dried leaves of *Pogostemon cablin*. It is dark yellow or orange colored viscous oil (Specific gravity: 0.970-0.990 at 15° C.), having strong fixative properties.

Conventional extraction for patchouli oil includes steam distillation and carbon dioxide (CO2) extraction methods.

It is well known to those skilled in the art that a slight increase in alcohol content is obtained when extracted oil is added to microbial culture and allowed to undergo biotransformation. However, the chances of reduction in yields and formation of byproducts increases in such process. The process is not economically feasible since the maximum oil concentration that can be added, as a substrate for biotransformation is limited due to toxicity problems.

Conventional techniques for increasing the patchulol content in patchouli oil by way of biotransformation is done by subjecting the substrates such as extracted components and also the whole oils to microbial or enzymatic action for alterations in their compositions. However, biotransformation technique is associated with drawbacks. By-product formation and the toxicity posed by the substrate and product to the microbial cells reduces the process effectively. Due to the significant presence of the by-products, the process steps to remove these products decreased the yield of the patchouli oil. Continuous agitation during biotransformation may cause volatilization of essential oil components resulting in lower product formation.

Looking to the need of the hour, the inventors have developed an improved process for increasing the patchulol content with the help of specific microbial cultures isolated from the soil. The reaction occurs under specific conditions of temperature and moisture.

As disclosed in U.S. Pat. No. 4,037,609, tobacco was subjected under controlled conditions, to the action of a microorganism effective to degrade nicotine through a biochemical reaction in which 3-succinoylpyridine formation was detected. Prior to subjecting the tobacco to the action of the microorganism, the tobacco is steamed to increase its moisture content. Tobacco treated in accordance with this process, when incorporated into a tobacco-smoking product, produces a mild smoke, having reduced nicotine content. However, there is no loss of desirable flavor, taste and smoking properties. Moreover, U.S. Pat. No. 4,037,609 does not teach the use for enhancing the aromatic oil quality. The present invention relates to subjecting the naturally occurring material to microbial action under controlled conditions resulting in the increase of the patchouli oil content.

In accordance with the present invention there is provided a commercially viable process for increasing the patchulol content with the help of specific microbial cultures isolated from the soil. The present invention also provides no significant alteration in the oil yields, while the odor or aroma is enhanced due to the increased alcohol content. The present invention aims to focus on the use of microbial cultures and has provided optimal conditions for increasing the alcohol content during the extraction of the oil from dried leaves of Patchouli.

SUMMARY OF THE INVENTION

It is an object of the present invention to provide a method for extracting the essential oil from *Pogostemon cablin* with increased patchulol content.

It is an object of the invention to increase the flavor content of the essential oil.

Further it is an object of this invention to achieve the increase in patchulol content through a simple, cheap and economical process.

Still further it is an aim of the present invention to modify the conventional steam distillation process by introducing a step in which the dried leaves are blended with a microbial isolate prior to distillation It is an important object of the invention to use microorganisms that would be responsible in treating leaves of patchouli for increasing the alcohol content.

It is an important object of our invention to present a process without compromising the yields of the essential oil with the use of a microbial isolate which comprises the fungal species of genus *Trichosporon*.

It is an object of this invention to present a process without any loss of patchouli oil content due to volatilization during extraction process.

The present invention relates to an improved process of extracting patchouli oil with increased patchulol content, from dried leaves of patchouli plant for enhancement of odor or aroma properties of the essential oil.

In one embodiment, the present invention applies a microbial treatment which involves the use of a microbial culture to specifically increase the patchulol content of patchouli alcohol without changing any major components of the essential oil. While the patchulol content of patchouli oil is increased, the characteristic odor properties are retained.

In another embodiment, the present process can also be used for increasing alcohol content in essential oil of *Pogostemon cablin* with inherently lower patchulol content. In such process the flavour of patchouli oil could significantly be improved by the microbial treatment of the present invention.

In one embodiment the present invention provides a process for enriching the odor profile of the patchouli oil. The present invention particularly alters or provides an increased alcohol content in the patchouli oil, thereby increasing the odor profile.

In another embodiment the present invention provides an process for improving the alcohol content which is simple, economical and scalable process.

Further, the present invention discloses the preparation of blend that signifies the reaction setup which could be in a way suitable for the microbial enzymatic action on the intracellular oil content. The physical conditions in the blend are optimized in the present invention so that the optimal activity of enzymes in microbial cells could be expressed.

The increase in patchulol content is marginally higher when the steam extract obtained from the leaf blend is directly added to the cultured isolate. These observations can be attributed to the fact that in the isolated state of the oil, lack of natural cofactors required for enzymatic activity by the microbial isolate would not be present.

BRIEF DESCRIPTION OF THE FIGURES

The following drawings form part of the present specification and are included to further demonstrate certain aspects of the present disclosure, the inventions of which can be better understood by reference to one or more of these drawings in combination with the detailed description of specific embodiments presented herein.

FIG. 3 is a gas chromatograph indicating the patchouli alcohol peak of the sample A (substrate).

FIG. 6 is a gas chromatograph indicating the patchouli alcohol peak of the sample B (biotransformed product).

DETAILED DESCRIPTION OF PREFERRED EMBODIMENTS

Figure 1:
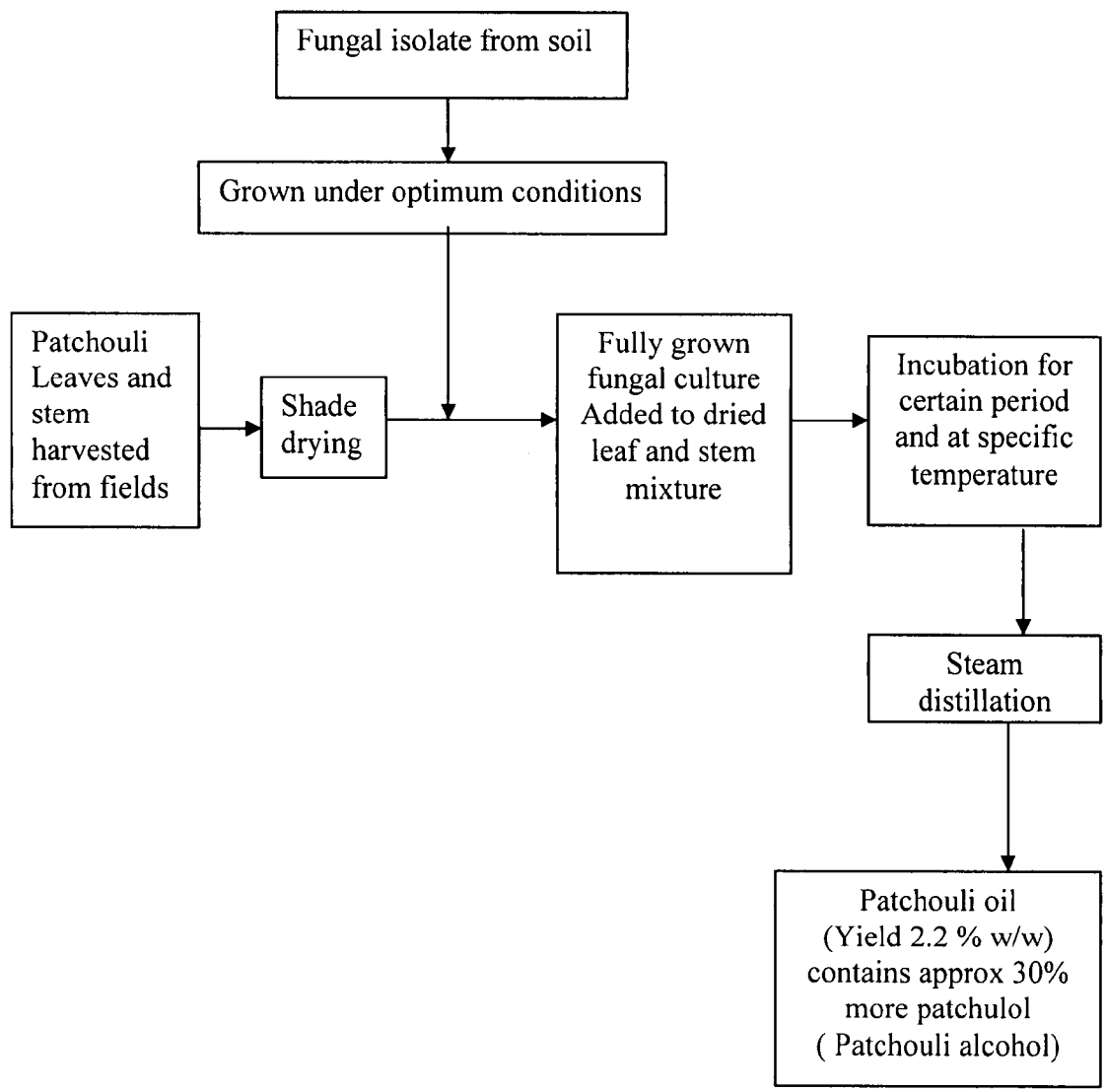
FIG. 1 is a schematic representation or flow diagram depicting the process for increasing the patchulol content with the help of specific microbial cultures isolated from the soil according to one embodiment of the present invention.

The present invention relates to an improved process of extracting patchouli oil with increased patchulol content, from dried leaves of patchouli plant for enhancement of odor or aroma and flavor properties of the essential oil of patchouli.

DEFINITIONS

Terms used in the invention are defined as follows:

The term "microbial treatment" as used herein refers to subjecting dried patchouli leaves (biomass blend) to an optimally grown microbial culture under controlled conditions.

The term "essential oil" as used herein refers to a volatile oil which is a water-immiscible liquid produced by distillation from plant material that is used in perfumes, cosmetics, incenses, and in medicine.

The term "biomass blend" as used herein refers to plant parts such as leaves from which one can extract the essential oil.

The term "bioconversion" as used herein refers to the process that employs microbial cells for converting substrates into products.

The term "biotransformation" as used herein refers to any chemical conversion of substances that is mediated by living organisms or enzyme preparations derived therefrom.

The present invention provides a novel method for extraction of patchouli oil comprising a step of microbial treatment of a patchouli biomass blend comprising patchouli leaves and stems, with a microbial culture.

In one embodiment, the microbial treatment is conducted prior to extraction of patchouli oil. In another embodiment, the microbial treatment is conducted on extracted patchouli oil.

The present invention relates to the surprising discovery that microbial treatment of a patchouli biomass during the oil-extraction process results in increased patchouli alcohol (patchulol) content in the extracted patchouli oil. The increased patchulol content results in enhancement of the sensory properties (e.g., odor or aroma, flavor, etc.) of the extracted oil.

In accordance with the present invention, microbial treatment comprises use of a microbial isolate for increasing the patchouli oil content. This isolate is selected from the group consisting of fungal, yeast and bacterial species of genus: *Aspergillus, Penicillium, Trichosporon, Rhizopus, Candida, Rhodotorula, Saccharomyces, Pseudomonas,* and *Bacillus*.

The microbes—fungi, yeast or bacteria—used for increasing patchulol content may be added as soil isolates or as propagated cultures of the microbes.

In one embodiment the present invention uses a microbial isolate from soil. The isolate is identified as fungal species of the genus *Trichosporon* which is responsible for specifically increasing the patchouli content and also the total oil content. The isolate has been identified as MTCC 7632.

A deposit of the *Trichosporon* spp. MTCC 7632 of Reliance Life Sciences, disclosed above and recited in the appended claims has been made with the Microbial Type Culture Collection, Institute of Microbial Technology, Sector 39-A, Chandigarh-160036 (India). The date of certification of deposit was Feb. 2, 2006. The deposit of *Trichosporon asteroides* spp. MTCC 7632 is the same deposit maintained by Reliance Life Sciences since prior to the filing date of this application. All restrictions upon the deposit have been removed, and the deposit is intended to meet all the requirements of 37 C.F.R. §1.801-1.809. The MTCC accession number is MTCC 7632. The deposit will be maintained in the depository for a period of 30 years, or 5 years after the last request, or for the effective life of the patent, whichever is longer, and will be replaced as necessary during that period.

The actual process comprises of component transformation catalyzed by certain microorganisms. The members of *Trichosporon* species are isolated from soil, water samples, vegetables, mammals, and birds. As well as being a member of the normal flora of mouth, skin and nails, it is the causative agent of superficial and deep infections in humans. The genus *Trichosporon* is non- or weakly fermentative. There is no sexual reproduction phase, but the fungus has a basidiomycetous affinity (Collier et. al; Larone).

Regarding the marginal increase in the total oil content, it can be explained that optimum oil extraction also depends upon the release of the amassed essential oil in the pectin cell wall of the stems and leaves which is then extracted by condensing the vapor emerging out of the distillation set up. The optimum release of oil can be facilitated by the use of enzymes, namely pectinases. In the present invention, *Trichosporon asteroides* was found to secrete similar enzymes that would ultimately aid in releasing the oil from the pectinic cell walls of the plant.

As described in U.S. Pat. No. 6,338,861 by Gozu et al (2002), an "unicellularized plant" is used as the starting material for a natural flavor or fragrance for developing and improving a natural flavor or fragrance. This patent describes applying an enzymatic treatment or chemical treatment or to shorten the aging period for producing the natural flavor or fragrance. The importance of aging for producing improved odor or aroma properties has been emphasized. The significance of applying pectinases for breaking down cell walls to increase release of flavor component has also been noted in the above patent.

The present invention included checking the isolate cultured by solid state fermentation for expression of pectinases whose presence was detected in the microbial culture. Thus the increase in oil content as compared with the blend from which oil was extracted without microbial treatment indicated the possibility of pectinase activity.

In accordance with the present invention, the improved methods of extraction may result in increasing the alcohol content in patchouli oil by a possible bioconversion reaction of certain substrates present as components of patchouli oil into the product patchouli alcohol or patchulol.

Without being bound by theory, it is postulated that enzymes present in a microorganism may be responsible for increase of alcohol in patchouli oil. Some enzymes known to be responsible for increasing the alcohol content during biotransformations are alcohol dehydrogenase type of enzymes. For example, biotransformation of benzaldehyde to L-phenylacetylcarbinol (L-PAC) as a key intermediate for L-ephedrine synthesis has been studied using *Candida utilis*. (Shin et al: 1995 Appl Microbiol Biotechnol; 44: 7-14). Gutierrez et al 2002. 98, 327-340 describes alcohol dehydrogenase catalyzed reduction of furfural to furfuryl alcohol by ethanologenic strains of bacteria. Nuñez et al, 207-212. describes $NAD^+$ as the cofactor required for the action of alcohol dehydrogenases.

The inventors of the present invention have found through experimentation that adding extracted oil to the microbial culture is less efficient.

Without being bound by theory, the increase in patchulol content in the present invention may be attributed to microbial enzymes and co-factors present as a part of the patchouli biomass blend.

In accordance with the present invention, methods for extracting patchouli oil with increased alcohol content, from dried leaves of patchouli plant for enhancement of flavor of the essential oil and analysis of the product, comprises some or all of the steps of: a) collection and drying of the patchouli leaves and stem mixture; (b) treatment of the dried leaves and stem mixture with microbial culture; (c) incubation; (d) extraction and distillation; and (e) analysis. Steps (b), (c) and (d) may be carried out in any particular order.

In accordance with the methods of this invention, the patchulol concentration in patchouli oil obtained after incubations with microbial isolates can be about 34%, 35%, 36%, 37%, 38%, 39%, 40%, 42%, 45% or more w/w.

Conventional extraction for patchouli oil includes steam distillation and carbon dioxide ($CO_2$) extraction methods.

Steam distillation is most commonly used method for extraction of the essential oil of patchouli. The leaves are shade dried and partially fermented before distilling. Fresh patchouli essential oil has a sharp, green fragrance, and needs to age to develop the deeper, earthier aroma of good patchouli oil. The color of the oil deepens from a light yellowish, pale red to deep, dark amber upon aging, and the oil becomes more and more viscous.

Patchouli oil can also be produced through the $CO_2$ extraction method. This is a new technique for extracting essential oils (and other constituents) from plant materials. It does not use water or steam. Instead $CO_2$ (carbon dioxide) is used as a solvent. The $CO_2$ is used under high pressure in which it expresses a likeness to both a gas and a liquid (called a supercritical state). These qualities allow the aromatic constituents of patchouli to be extracted without heat. The $CO_2$ is then removed from the resulting extract, which is then refined and filtered. The oil produced from this method has a different odor profile than the oil obtained by steam distillation. $CO_2$ extracts are still relatively rare due to the large cost in setting up the equipment. However, the method requires a careful monitoring of the in process pressure of $CO_2$ and end process controls for removing the $CO_2$.

Since the steam distillation is the preferred method of use, attempts are usually made in improving the alcohol content of the essential oil prior to the extraction by steam distillation process. A vacuum distillation unit is the preferred method of use for extraction of oil at the laboratory level.

EXAMPLES

The following examples are included to demonstrate preferred embodiments of the invention. It should be appreciated by those skilled in the art that the techniques disclosed in the examples which follow represent techniques discovered by the inventor to function well in the practice of the invention, and thus can be considered to constitute preferred modes for its practice. However, those skilled in the art should, in light of the present disclosure, appreciate that many changes can be made in the specific embodiments which are disclosed and still obtain a like or similar result without departing from the spirit and scope of the invention.

Example 1

Collection and Drying of the Patchouli Leaves and Stem Mixture

In the present invention, harvesting of patchouli leaves was done after 12-14 weeks with utmost care so as to obtain highest oil yields of patchouli. It is a known fact that oil is present in all parts of the patchouli plant, however high oil content is found in the leaf portion of the plant. In the present extraction process, the top leaves were cut during the harvesting season. The leaves were dried for three days by laying it on cement surface in the shade. By drying in the shade reduces the loss of oil by evaporation as compared to drying under the sun. Proper care was taken to completely dry the leaves to prevent the mold formation and subsequent loss of oil.

Example 2

Isolation of Microbial Cultures for Conducting Biotransformations

The isolation of a microbial culture isolate is conducted by serial dilutions of various soil samples in sterile saline (0.85% w/v) solution. The saline dilutions were selectively sub-cultured on ampicillin sodium salt (300 ppm) containing nutrient medium (Modified Sabouraud Dextrose medium; Peptone 1% w/v; Dextrose 2% w/v; Yeast extract 0.5% w/v: pH 5.5) for isolation of fungal and yeast species. The dilutions were repeatedly subcultured on nutrient agar plates containing 5-25 ppm cycloheximide for isolation of bacterial cultures. Repeated subculturing for at least 3 times in presence of specific selective inhibitors resulted in the isolation of pure microbial cultures. On obtaining various microbial isolates, these were grown in media that was optimally supplied with nutrients (MGYP: Malt extract 0.3% w/v; Yeast Extract 0.5% w/v; Glucose 1% w/v; Peptone 0.3% w/v pH 5.5) under controlled conditions of temperature (28° C.-38° C.).

Example 3

Treatment of Extracted Oil of *Pogostemon cablin* With Microbial Cultures

The microbial isolates on obtaining optimum turbidity in the flasks containing nutrient medium, were allowed to conduct biotransformation with addition of extracted patchouli oil. The concentration of substrate (patchouli oil) added was 0.1% w/v-2% w/v and common for all the isolates.

Example 4

Incubation and Extraction of The Oil

The flasks containing the reaction mixture were incubated at temperatures of 28-40° C. for a period of 24 H-72 H. Timely analysis of the oil added to fungal cultures was carried out by taking out samples after every eight-hour interval. The reaction mixture was treated with double the volumes of petroleum ether (40° C.-60° C.). The reaction mixture along with the treated solvent was allowed to separate for 30 minutes in a separating funnel. The bottom layer containing the aqueous phase was drained off. The oil added to the fungal culture medium would get extracted in the organic solvent phase and remain in the upper layer. The top layer was separated in a dry flask. 1% w/v Sodium Sulphate was added to the organic phase to remove traces of moisture from the aqueous phase. Such a treated organic solvent containing the essential oil was subjected to vacuum distillation in a Buchi Rotavapor distillation unit. The conditions for Buchi Rotavapor (R-205) operation were: Water bath temperature: 70-100° C.; Vacuum applied 300-700 mbar; duration; 30 min-120 min).

Example 5

Analysis of The Distilled Oil

On completion of vacuum distillation, the organic phase was separated in the collection flask and the essential oil residue remained in the distillation still. This was collected by addition of petroleum ether and stored. The weight of the residual oil was estimated. The ratio of substrate added and product obtained on weight basis was determined by comparing the weights of the two samples. The contents of the residue were analyzed by gas chromatography (Model: Nucon; Column—Agilent HP-5 (L: 39 m, I.D: 0.32 mm). Initial oven temperature: 40° C. Final oven temperature: 270° C. Gas Flow rates: Hydrogen—30 ml/min; air—300 ml/min; nitrogen—2-8 ml/min: column; 30 ml/min: Detector). The results of the extracted oil (FIG. 3) were compared with the GC-MS report of the substrate (patchouli) where the patchulol peak was identified. (FIG. 6).

Figure 2:
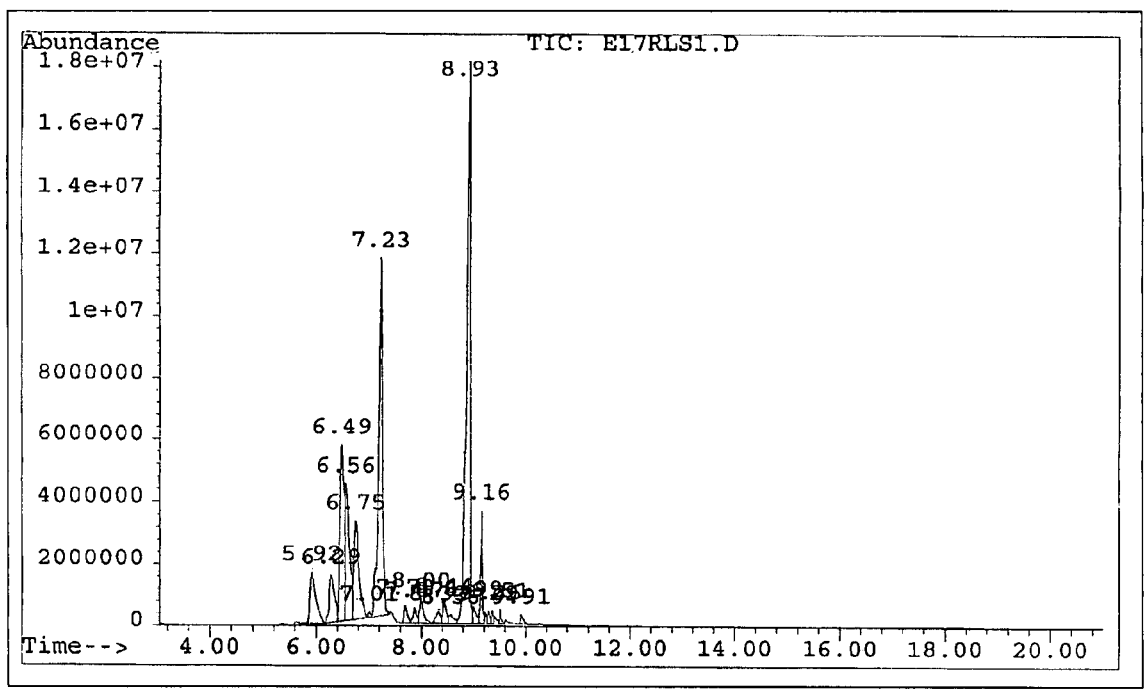
FIG. 2 is a gas chromatograph of the sample A (substrate).
Figure 4:
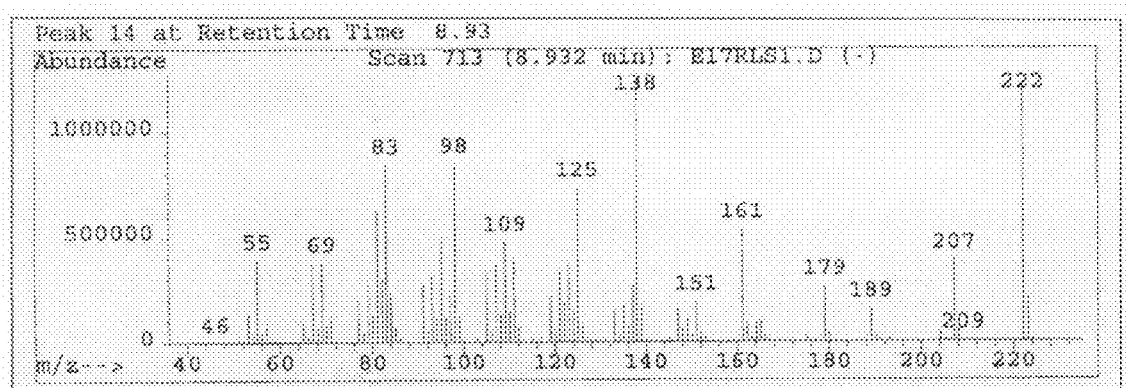
FIG. 4 is a report of mass spectroscopy for identification of patchulol peak in Sample A (substrate).
Figure 5:
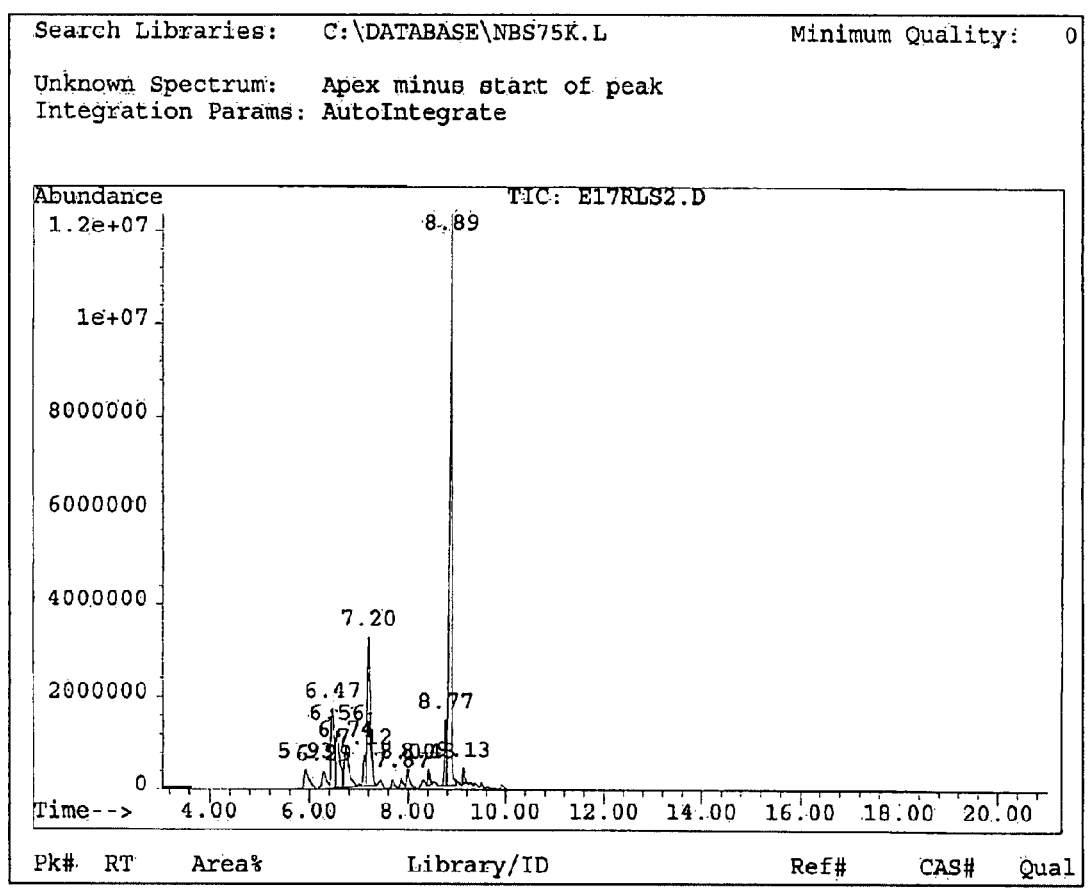
FIG. 5 is a gas chromatograph of the sample B (biotransformed product).
Figure 7:
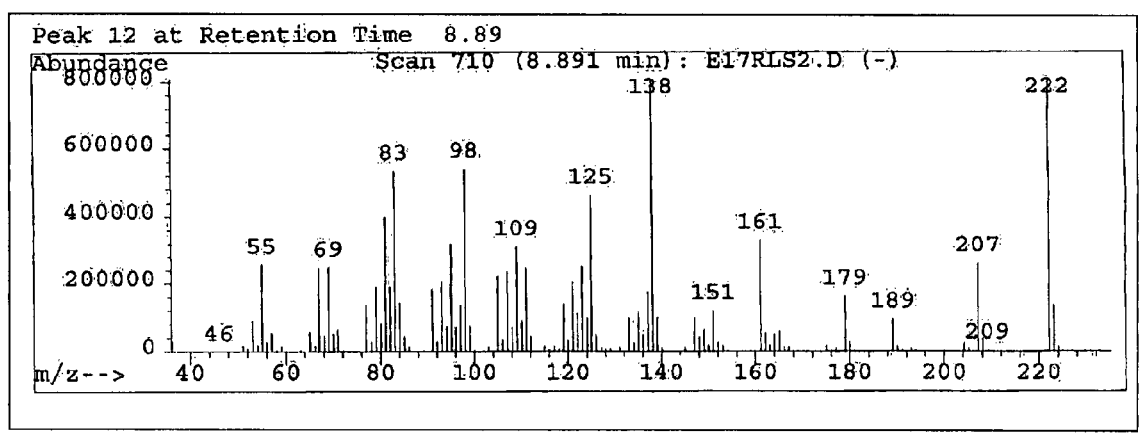
FIG. 7 is a report of mass spectroscopy for identification of patchulol peak in sample B (biotransformed product).

The increase in the patchouli alcohol (patchulol) content was estimated by determining the peak area percentages at equal concentrations for all the samples. The selection of particular microbial isolate for increasing the patchulol content was based on the GC results indicating significant increase in the patchulol content. (FIGS. 2 and 5). The identification of compound peaks was also confirmed by Mass Chromatography (FIGS. 4 and 7).

Among the various microbial isolates, certain isolates showed a 30% increase in the patchulol content. The original patchulol content in the substrate was estimated and found to be 33% v/v (approx). On biotransformation with the particular isolate, the patchulol content increased to 45% v/v.

Optimum growth conditions for these particular isolates were determined. The temperature and pH optima of 28-40° C. and pH=4-7 were found to be suitable for the growth of these isolates.

Example 6

Effect of Incubation Conditions with Microbial Cultures On The Oil Content

The effects of particular isolates on leaves (in situ) were determined. In the present process, dried leaves and stem mixture weighing 80 g were taken in 5 flasks. The moisture content of leaves and stem matter after drying was reduced to 1% w/w. The process for preparing the mixture with the microbial culture included addition of the optimally grown microbial culture (250 ml) with the leaves and stem matter and proper mixing of the same. The mixture was later incubated in a closed container at 28° C.-38° C. for periods of 24, 48, 72, 96 and 120 hrs. The moisture content of the mixture was estimated and found out to be 15% w/w approximately. After every 24 hour interval, each flask containing 80 g leaves treated with pre-grown fungal culture was subjected to distillation in the Rotavapour equipment using the conditions mentioned earlier. The patchouli oil quantity obtained after distillation was 2.2% w/w. GC analysis of the residual oil was done. The patchulol content of the oil extracted on each day for 5 days was estimated. The patchulol content of the oil extracted from leaf and stem mixture incubated for 24 hours was the highest. A significant increase of up to 30% was obtained on the first day. However, there resulted a gradual decrease on the $2^{nd}$ and $3^{rd}$ day of incubation. The patchulol increase was calculated to 20% and 15% respectively. However a gradual increase in the patchulol content was observed on the $4^{th}$ and the $5^{th}$ day. The patchulol content improved to 20% and 27% on the $4^{th}$ and $5^{th}$ day respectively. The experimentation was repeated several times and similar results were obtained.

| Sr. No. | Incubation time(hours) | Increase in patchulol content (%) |
| --- | --- | --- |
| 1 | 24 | 30 |
| 2 | 48 | 20 |
| 3 | 72 | 15 |
| 4 | 96 | 20 |
| 5 | 120 | 27 |

Example 6

Scale Up Process Of Extraction

Similar experimentation was repeated on a larger scale. Dried leaves and stem mixture weighing 400 g were ground to reduce the particle size to approximately 2 cm. The moisture content of leaves and stem matter after drying was reduced to 1% w/w. The process for preparing the mixture with the microbial culture included addition of the optimally grown microbial culture (1,250 ml) with the leaves and stem matter and proper mixing of the same. The mixture was later incubated in a closed container at 28° C.-38° C. for a period of 24 h. The moisture content of the mixture was estimated and found out to be 15% w/w. After every 24 h interval, the mixture was subjected to distillation in the Rotavapour equipment using the conditions mentioned earlier. The patchouli oil quantity obtained after distillation was 2.2% w/w. Gas chromatography (GC) analysis of the residual oil was done. GC analysis results indicated increased concentrations of patchouli alcohol. A 30% increase in patchouli alcohol was obtained. The initial patchouli alcohol concentration in standard patchouli oil was 33% w/w. On treatment of leaves with the microbial isolate, the patchouli alcohol concentration increased to 45% w/w.

All publications, patents and patent publications mentioned in this specification are herein incorporated by reference into the specification in their entirety for all purposes.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the methods described herein without departing from the concept, spirit and scope of the invention.

More specifically, it will be apparent that certain agents that are chemically or physiologically related may be substituted for the agents described herein while the same or similar results would be achieved.

Although the invention has been described with reference to preferred embodiments and examples thereof, the scope of the present invention is not limited only to those described embodiments. As will be apparent to persons skilled in the art, modifications and adaptations to the above-described invention can be made without departing from the spirit and scope of the invention, which is defined and circumscribed by the appended claims.

We claim:

1. A method for preparing a patchouli biomass for extraction of patchouli oil with increased patchulol content, the method comprising:
    a. providing a dried patchouli biomass;
    b. contacting the dried patchouli biomass with a microbial culture, wherein the microbial culture comprises *Trichosporon asteroides* or *Trichosporon* spp. MTCC 7632;
    c. incubating the dried patchouli biomass with the microbial culture under conditions and for a period of time sufficient to increase the amount of patchulol in patchouli oil contained in said patchouli biomass; and
    d. recovering said incubated biomass, wherein the patchouli oil when extracted from said incubated biomass has increased patchulol content.

2. The method of claim 1, wherein in step (c) the incubating with the microbial culture increases the amount of the patchulol in the patchouli oil by 33% to 45% w/w.

3. The method of claim 1, wherein the dried patchouli biomass has moisture content below 1% w/w.

4. The method of claim 1, wherein the microbial culture is a propagated culture.

5. The method of claim 1, wherein the microbial culture is a soil isolate.

6. The method of claim 1, wherein the incubating of the dried patchouli biomass with the microbial culture comprises incubating for at least 24 hours.

7. A method for extraction of patchouli oil with increased patchulol content, the method comprising:
    a. incubating a dried patchouli biomass with a microbial culture under conditions and for a period of time sufficient to increase the patchulol content in the patchouli oil contained in said dried patchouli biomass, wherein the microbial culture comprises *Trichosporon asteroides* or *Trichosporon* spp. MTCC 7632; and
    b. extracting the patchouli oil from the incubated patchouli biomass, wherein the patchouli oil extracted from said incubated biomass has an increased patchulol content relative to the patchouli oil content in the dried patchouli biomass prior to incubating with the microbial culture.

8. The method of claim 7, wherein in step (b) the extracting of the patchouli oil further comprises:
    i. adding a water immiscible organic solvent to an incubation mixture of the patchouli biomass and the microbial culture;
    ii. separating an organic phase containing the patchouli oil and the organic solvent; and
    iii. removing the water immiscible organic solvent.

9. The method of claim 7, wherein the extracting comprises steam distilling.

10. The method of claim 7, wherein the extracting comprises carbon dioxide ($CO_2$) extracting.

11. The method of claim 7, wherein the incubating comprises incubating at a temperature between 20° C. to 30° C.

12. The method of claim 7, wherein the incubating of the dried patchouli biomass with the microbial culture comprises incubating for at least 24 hours.

13. The method of claim 7, wherein the patchouli biomass comprises leaves and stems of *Pogostemon cablin*.

14. The method of claim 7, wherein a patchulol content of the patchouli oil extracted is at least 10% greater than a patchulol content of patchouli oil extracted without incubating with the microbial culture.

15. The method of claim 14, wherein the patchulol content of the patchouli oil extracted is at least 15% greater than the patchulol content of patchouli oil extracted without incubating with the microbial culture.

16. The method of claim 7, wherein the patchulol concentration of the extracted patchouli oil is at least 35% w/w.

17. The method of claim 7, wherein the patchulol concentration of the extracted patchouli oil is at least 45% w/w.

18. The method of claim 7, wherein the patchulol concentration of the extracted patchouli oil is at least 55% w/w.

19. A method for preparing patchouli oil with increased patchulol content, the method comprising:
    a. extracting patchouli oil from a dried patchouli biomass;
    b. incubating the extracted patchouli oil extracted from the dried patchouli biomass with a microbial culture under conditions and for a period of time sufficient to increase the patchulol content in the extracted patchouli oil, wherein the microbial culture comprises *Trichosporon asteroides* or *Trichosporon* spp. MTCC 7632; and
    c. recovering the patchouli oil having increased patchulol content.

20. The method of claim 19, wherein the extracting comprises steam distilling.

21. The method of claim 19, wherein the extracting comprises carbon dioxide ($CO_2$) extracting.

22. The method of claim 19, wherein the patchouli biomass comprises leaves and stems of *Pogostemon cablin*.

23. The method of claim 19, wherein the patchulol content of the patchouli oil is at least 30% greater than a patchulol content of patchouli oil not incubated with the microbial culture.

24. The method of claim 19, wherein the patchulol concentration of the recovered patchouli oil is at least 45% w/w.

* * * * *